United States Patent
Zamoyski

(10) Patent No.: US 7,309,486 B1
(45) Date of Patent: Dec. 18, 2007

(54) HER CANCER PROTOCOLS

(76) Inventor: Mark Zamoyski, 988 Foothill Dr., San Jose, CA (US) 95123

(*) Notice: Subject to any disclaimer, the term of this patent is extended or adjusted under 35 U.S.C. 154(b) by 809 days.

(21) Appl. No.: 10/295,600

(22) Filed: Nov. 15, 2002

(51) Int. Cl.
*A61K 39/00* (2006.01)
*A61K 39/395* (2006.01)

(52) U.S. Cl. .................... 424/130.1; 424/198.1

(58) Field of Classification Search .............. None
See application file for complete search history.

(56) References Cited

FOREIGN PATENT DOCUMENTS

WO    WO 96/40284    * 12/1996

OTHER PUBLICATIONS

Jain, Scientific American, 1994, vol. 271, pp. 58-65.*
O'Quinn et al (Gynecologic Oncology, 1984, vol. 18, pp. 135-144).*
the abstract of Rossi et al (Blood, 2000, vol. 96, pp. 326a-327a).*
Aglietta et al (Leukemia. 1991 vol. 11, pp. 979-984).*
Pegram et al. Oncogene, 1999, 18, 2241-2251.*
Barranco et al (Cancer Research, 1982, vol. 42, pp. 2899-2905).*
Bunn et al, Clinical Cancer Research, Oct. 2001, vol. 7, pp. 3239-3250.*
Cooper, "Oncogenes", 1995, p. 203.*
Herceptin (trastuzumab) Full Prescribing Information, Nov. 2006 Revision, Genentech Inc.
Harrison's Principles of Internal Medicine, Braunwald et. al., 15th edition, McGraw Hill, 2001, pp. 530-531, 538-541.
Harrison's Principles of Internal Medicine, Fauci et. al., 14th edition, McGraw Hill, 1998, pp. 527-536.
Molecular Biology of the Cell, Alberts et. al. Third Edition, Garland Publishing, 1994, pp. 896-897, 898.
Herceptin® Trastuzumab, Full Prescribing Information, Genentech, Inc., FDA revision Aug. 2002.
Zamoyski, Mark, "Cell Cycle Synchronous Chemotherapy", presentation / seminar handout at Stanford Genome Technology Center, 855 California Ave, Palo Alto, CA, Sep. 2, 2004.
Science News, Aug. 11, 2001 vol. 160, p. 89, "Chemotherapy leads to bone loss" by Damaris Christensen.
Fonagy et. al., "The effect of . . . galactitiol on RNA synthesis . . .", Acta Biochim Biophys Acad Sci Hung., 1981; 16(3-4):151-62.

* cited by examiner

*Primary Examiner*—Karen A. Canella

(57) ABSTRACT

The present invention discloses protocols for HER cancers that are also endocrine dependent in a manner that provides dual action by using both HER antibodies and endocrine blockers/downregulators and insures function of S-Phase cytotoxics by administration of endocrines prior to administration of the S-Phase cytotoxic.

4 Claims, 9 Drawing Sheets

Sweep 1 - Day 0
S-Phase Chemo

Sweep 1 - Day 3.5
Cytostatic + S-Phase Chemo

Sweep 1 - Day 6
S-Phase Chemo

Sweep 1 - Day ≥ 17
and Sweep 2 - Day 0

Sweep 2 - Day 1
S-Phase Chemo

Sweep 2 - Day 2
S-Phase Chemo
+ Cytostatic

Sweep 3 - Day 0

Sweep 3 - Day 2.5
S-Phase Chemo + Cytotstatic

Sweep 3 - Day 4

HER CANCER PROTOCOLS

CROSS REFERENCE TO RELATED APPLICATIONS

This application is related to application Ser. No. 09/991,427 filed Nov. 16, 2001, which disclosed that prior art phase specific chemotherapeutic regimens fail to maintain phase synchronicity with cancer cell populations because of chemothrapetuic induced Gompertzian acceleration and additionally, in endocride dependent cancers, because of phase distortions and cell cycle accelerations caused by normal fluctuations of indigenous endocrine levels. Application Ser. No. 09/991,427 provided novel methods of preventing this asynchronicity in endocrine dependent cancers, using endocrine blockers and endocrine accelerants to "stop" and "start" the cancer cell cycle, in conjunction with administration of cytotoxic chemotherapeutics, so that the susceptible phase in the cancer cells remained synchronized to subsequent administration of phase specific cytotoxic chemotherapeutics.

Present application teaches how to maintain phase synchronicity in non endocrine dependent cancers. Novel chemotherapeutic regimens are also disclosed. "Conforming Regimens" are disclosed for use prior to chemotherapeutic regimens. Conforming Regimens insure a uniform cell cycle rate across all cancer cells allowing the subsequent chemotherapeutic regimen to avoid Gompertzian related failure. Phase Compressing Chemotherapeutic Regimens are also disclosed which greatly reduce the number of cytotoxic administrations required over prior art while also boosting curative probabilities and preventing inter administration cycle regrowth related failures.

STATEMENT REGARDING FEDERALLY SPONSORED RESEARCH

Not Applicable.

INCORPORATION-BY-REFERENCE OF MATERIAL SUBMITTED ON A CD

Not Applicable

BACKGROUND OF THE INVENTION

1. Field of the Invention

The invention relates to composition and methods for the treatment of cancer.

2. Description of Related Art

Prior Art:

Currently, surgery accounts for around 80% of the curative benefit in the roughly 50% of people that survive cancer today. Chemotherapy and radiation account for the balance. The curative value of chemotherapy as used under prior art is minimal at best. Advanced stage cancers, which rely primarily on chemotherapy for a cure, indicate just how modest chemotherapy's contribution is under prior art: the 5 year survival rate for Stage 1V metastatic lung cancer is 1%, Stage 1V metastatic colon cancer is 5%, pancreatic cancer is 2%, and Stage 1V metastatic breast cancer is 14% (Harrison's 15th ed. pgs. 565, 584, 591, 575 respectively). Clearly, prior art is in dire need of curative chemotherapeutic regimens. The present invention provides them.

Harrison's Principles of Internal Medicine (14th ed. p. 527-536) outlines prior art chemotherapeutic drug treatments used for cancer.

Most chemotherapeutic agents in use today are cell cycle active; that is, they are cytotoxic mainly to actively cycling cells. In addition, most cell cycle active agents are phase specific; that is, they are cytotoxic to cells in a particular phase of the cell cycle. Of the 44 commonly used chemotherapeutics listed in Harrison's (15th ed.), more than 70% are phase specific, primarily S-phase specific.

Alkylating agents are among the most widely used anti tumor agents and are efficient at cross-linking DNA, leading to strand breakage. Alkylating agents include cyclophosphamide, ifosfamide, melphalan, busulfan, mechlorethamine (nitrogen mustard), chlorambucil, thiotepa, carmustine, lomustine as well as platinum compounds such as cisplatin and carboplatin, which are not true alkylating agents also lead to covalent cross linking of DNA. These agents are best regarded as cell-cycle active but non-phase specific.

Purine/pyrimidine analogs/antimetabolites induce cytotoxicity by serving as false substrates in biochemical pathways. They are cell cycle active and specific mainly for the S phase. They include cytarabine, fluorouracil, gemcitabine, cladribine, fludarabine, pentostatin, hydroxyurea, and methotrexate.

Topoisomerase inhibitors interfere with the enzymes topoisomerase 1 and topoisomerase 2, responsible for mediating conformational and topological changes in the DNA required during transcription and replication. These agents include daunorubicin, doxorubicin, idarubicin, etoposide, teniposide, dactinomycin, and mitoxantrone. They are S-Phase specific.

Plant Alkaloids include vincristine, vinblastine, and vinorelbine which inhibit microtubule assembly by binding to tubulin and docetaxel and paclitaxel which function by stabilizing microtubules and preventing their disassembly. They are cell cycle active and cytotoxic predominately during the M phase of the cell cycle.

Antitumor Antibiotics include bleomycin that induces DNA strand breakage through free radical generation and Mitomycin C which cross links DNA. They are cytotoxic mainly during the G2 and M phase.

Other Agents include dacarbazine and procarbazine which act as alkylating agents to damage DNA and L-Asparaginase, the only enzyme used as a anti tumor agent, which acts by depletion of extracellular pools of asparagine.

Therapeutic Index Dosaging:

Chemotherapeutic agents exhibit a dose response effect. At sufficiently low concentrations no cytotoxicity is observed. At increasing concentrations, cell kill is proportional to drug exposure. At high concentrations, the effect reaches a plateau. Drugs that are cell cycle active, but not phase specific, such as alkylating agents, characteristically have steep dose response curves: An increase in the drug concentration by an order of magnitude or more results in a proportional increase in tumor cell kill. By contrast, the dose response curve of phase specific agents, such as the antimetabolites, typically is linear over only a narrow range. These agents are less suitable for dose escalation and increased tumor cell kill is observed after prolonged exposure as a larger percentage of the tumor cells enter the cell cycle.

Chemotherapy employs two principles in administration: Therapeutic Index Dosaging and Cyclical Administration (HPIM 14th ed. 527-528 Pharmocodynamics section).

The therapeutic index represents the difference between the response of the tumor and response of normal tissue for a given dose of chemotherapeutic. Normal cells are also susceptible to the cytotoxic effects of chemotherapeutic drugs and exhibit a dose-response effect, but the response curve is shifted relative to that of malignant cells (see HPIM 14th ed. P. 528, FIG. 86-3 enclosed). This difference represents the therapeutic index. The toxicity to normal tissue that limits further dose escalation is the "dose-limiting toxicity". The dose just below this point is the "maximum tolerated dose". Proliferative normal tissues such as the bone marrow and gastrointestinal mucosa are generally the most susceptible to chemotherapy-induced toxicity. The usefulness of many chemotherapeutics is limited by the fact that they have a narrow therapeutic index.

Skipper Log Cell Kill Model

Tumor regression in response to chemotherapy is logarithmic. The "tumor kill rate" (TKR) as used in this application is hereby defined as the percentage of cells of a tumor that are killed during one administration cycle of a chemotherapeutic. The "phase kill rate" (PKR) as used in this application is hereby defined as the percentage of cells in a given phase of the cell cycle that are killed by a single administration of a phase specific chemotherapeutic. As an example, if a 99% S-phase kill rate chemo is administered, and 32% of the cells are in the S-phase, the tumor kill rate will be 31.7% (i.e. 0.99×0.32) if only one administration is given. If 4 administrations are given in a cycle and are rationally timed to the progression of new cells into the S-Phase, and the susceptible phase in the incoming batch of cancer cells remains synchronized to each chemotherapeutic administration, then the tumor kill rate will equal the phase kill rate.

Conventional methods typically focus on "maximum tolerated doses" and extended administration periods. Cyclical administration is required to allow normal rapidly proliferating cell populations to recover from the effects of chemotherapy. The number of administration cycles required to completely eradicate a tumor is dependent on the tumor kill rate of the therapeutic. To completely eradicate a tumor it is necessary to get below the mathematical 1 surviving cell number. As an example, to kill a 10 billion cell tumor with a chemotherapeutic that kills 95% of the tumor cells each administration cycle (5% survive) would require 8 cycles of chemotherapy (i.e. 10,000,000,000×0.05×0.05×0.05×0.05× 0.05×0.05×0.05×0.05=0.39). In contrast, a chemotherapeutic with a 50% tumor kill rate would require 34 administration cycles to get the 10 billion cell tumor below the one surviving cell number (i.e. 10,000,000,000×0.5 (34 times)=0.58). Likewise a 99% tumor kill rate would require only 6 administration cycles to get the 10 billion cell tumor below the one surviving cell number. The Skipper log cell kill model does not allow for tumor growth between administration cycles.

Combination Chemotherapy:

Under prior art most cancers are treated with combination chemotherapy (HPIM 14th ed. p. 531-532) in an attempt to boost curative result. The underlying principles are that 1) each agent should have an independent activity against a specific tumor, 2) each drug should have a different mechanism of action (MOA), 3) there should be no cross resistance among the agents used, and 4) each agent should have a different dose-limiting toxicity profile.

BRIEF SUMMARY OF THE INVENTION

The present invention provides two novel chemotherapeutic regimens that will yield curative result versus prior art's palliative results, and simultaneously lower systemic toxicity over prior art. Present invention synchronizes the susceptible phase in the cancer cells to administrations of phase specific chemotherapeutic and prevents asynchronicity arising from either chemotherapeutic induced Gompertzian acceleration, inter cycle regrowth, and indigenous endocrine oscillations (in endocrine dependent cancers), all of which have been ignored by prior art chemotherapeutic regimens.

The first method is termed a "Cancer Cell Cycle Time Conforming Regimen" or "Conforming Regimen" and relates to administration of one or more cycles of cytotoxic agents in conjunction with cytostatic agents in a manner that will insure a uniform cell cycle time by all cancer cells in response to a subsequent chemotherapeutic regimen. The "Conforming Regimen" is required for conventional chemotherapeutic regimens to work if there is one or more tumors which is greater than approximately 1 cc in size. The Conforming Regimen basically reduces a tumor's size to where it will cycle at its fastest possible rate, and holds the reduction in place until chemotherapy is initiated.

The second method termed "Phase Compressing Chemotherapy" relates to use of cytostatic agents in conjunction with cytotoxic agents in a manner that, with successive administrations, aggregates surviving cancer cells into a tight(er) band in a phase of the cell cycle, reducing the number of cytotoxic administrations required versus prior art, preventing inter cycle regrowth, and increasing the probability of curative outcome over prior art.

BRIEF DESCRIPTION OF THE DRAWINGS

FIGS. 7d-7i show the population phase distribution at selected points during two sweeps of a Phase Compressing Regimen.

DETAILED DESCRIPTION OF THE INVENTION

Background

To understand why present invention's "Conformed Chemotherapy" is curative, it is first necessary to understand why prior art's chemotherapeutic regimens are not curative.

Figure 1:
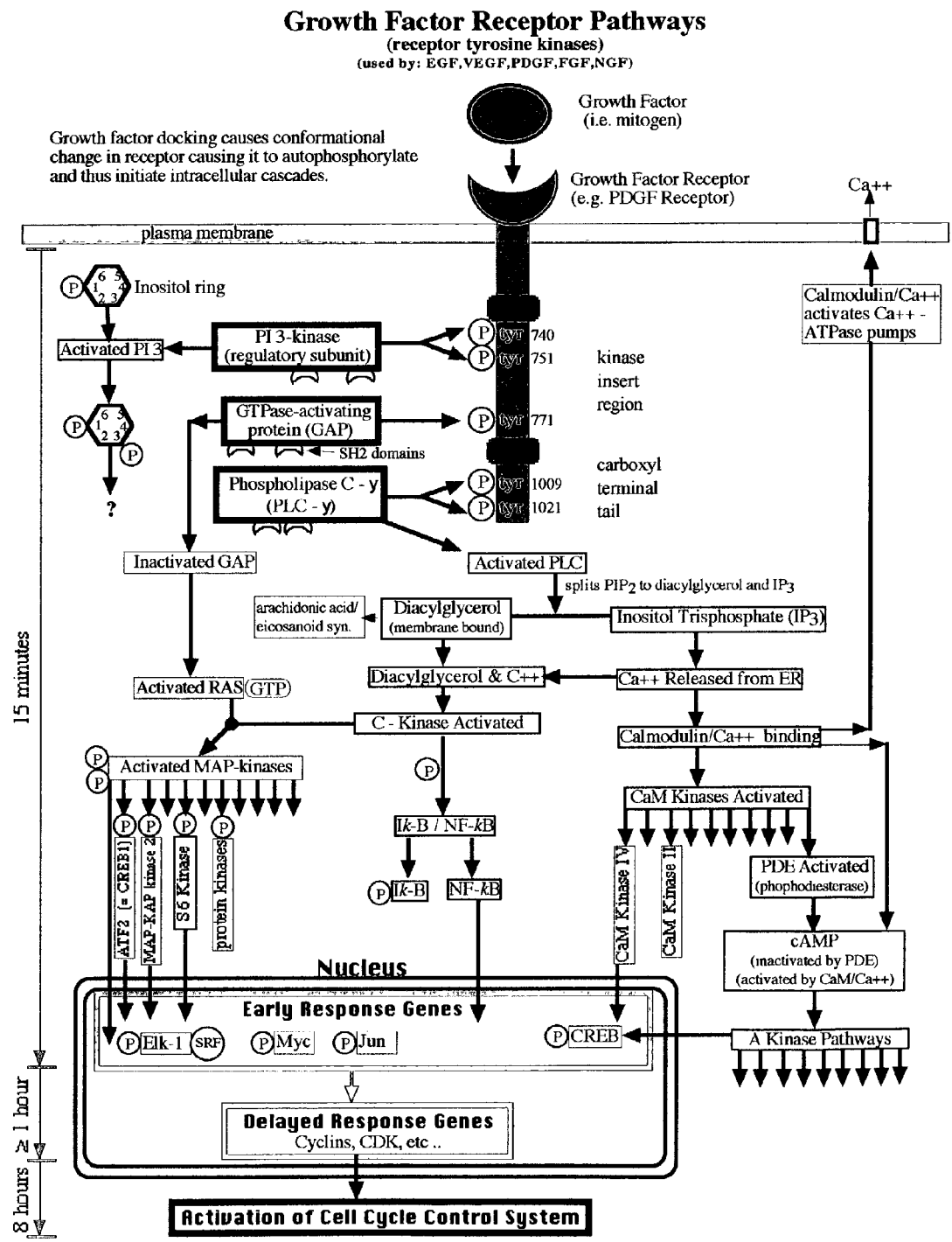
FIG. 1 shows the mitogen dependent biochemical pathways up until the activation of the cell cycle control system.
Figure 2A:
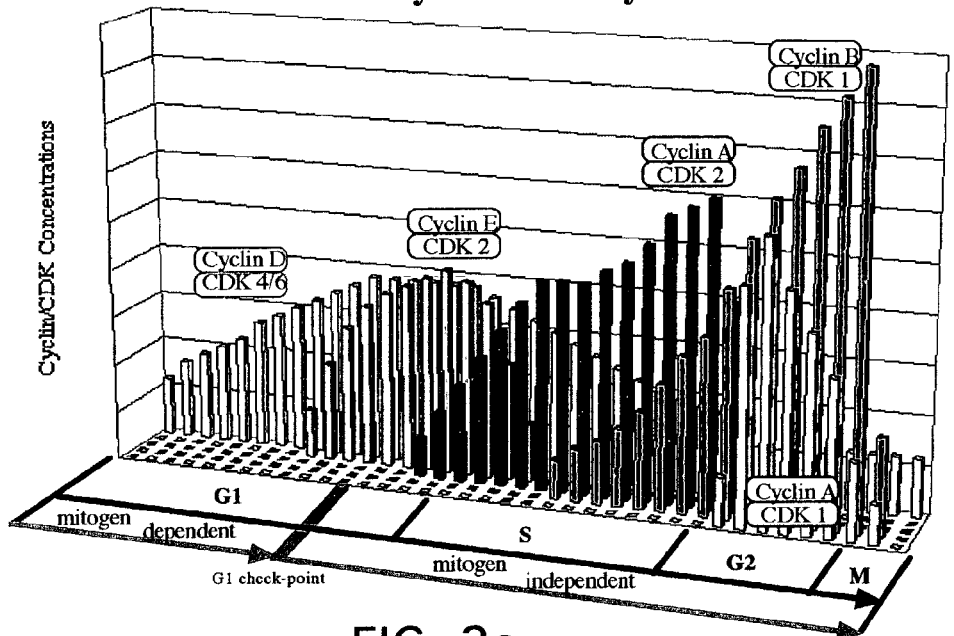
FIG. 2a shows the observable bursts of cyclin/cdk production associated with the cell cycle control system.
Figure 2B:
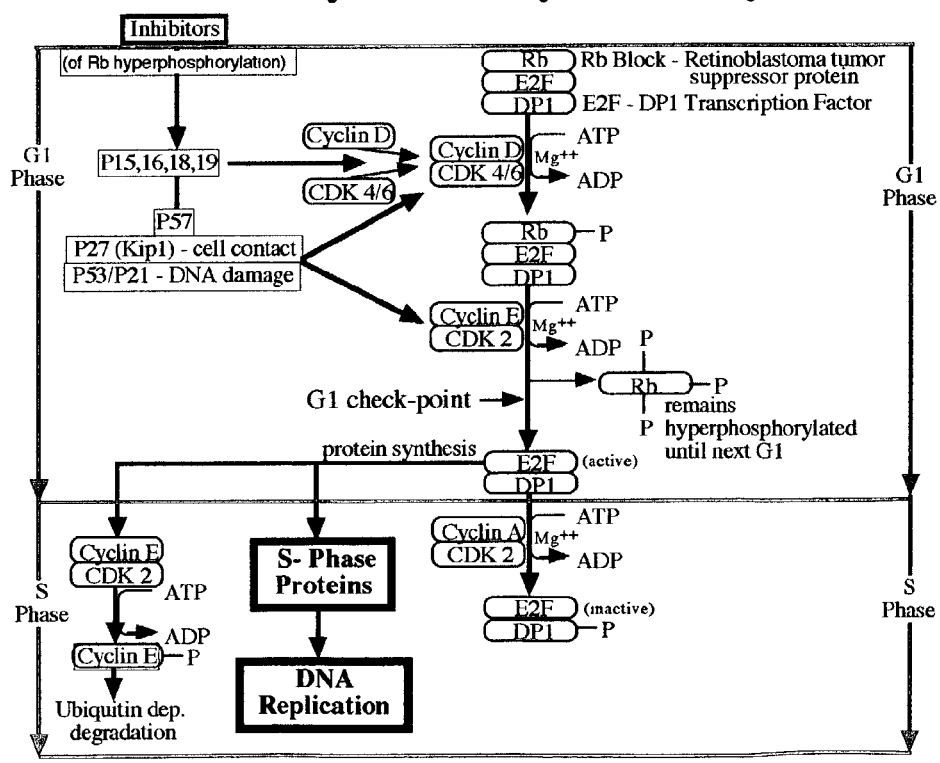
FIG. 2b shows the biochemical pathways affected by the cell cycle control system, from G0 through the S-Phase.

Cancer starts with a single aberrant cell that has accumulated several independent genetic accidents related to growth control. The single cancer cell, and all of its progeny, are genetically programmed or "hard wired" to relentlessly grow and divide. FIG. 1 and FIG. 2b show some representative pathways related to growth control. Cancer can occur from mutations in genes related to production of proteins used anywhere along the growth control pathways. These include: 1) overexpression or inappropriate expression of genes related to the production of growth factors, growth factor receptors, transduction molecules, and transcription molecules (collectively oncogenes), 2) underexpression or inappropriate expression of tumor suppressor genes, and 3) overexpression of telomerase (not shown).

If chemotherapy leaves even a single cancer cell alive, the cancer will recur. In application Ser. No. 09/991,427 filed Nov. 16, 2001, incorporated herein by reference, applicant disclosed why prior art phase specific chemotherapeutic regimens fail to yield curative result. The failure relates to the Gompertzian acceleration, or reduction in cancer cell cycle time, induced by the chemotherapeutic reduction of tumor size, which in turn results in the cancer's lack of phase synchronicity to subsequent administrations of the phase specific chemotherapeutic(s).

Figure 3:
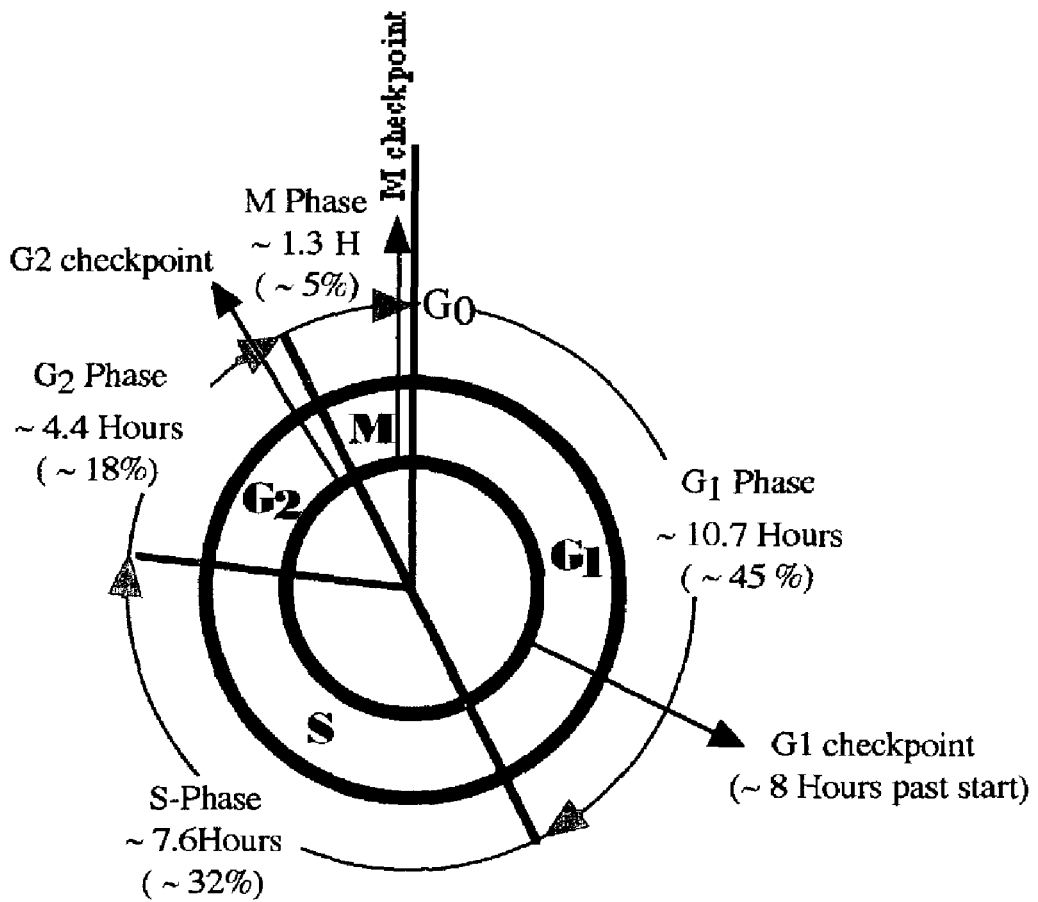
FIG. 3 shows the phase distribution and checkpoint locations for a typical cycling cell.

All dividing cells go through 4 distinct phases: G1 or growth phase, S or synthesis of DNA phase, G2 or growth 2 phase, and M or mitosis phase where the cell pulls apart into two cells. A normal actively dividing cell spends approximately 45% of its time in the G1 Phase, 32% in the S Phase, 18% in the G2 Phase and 5% of its time in the M Phase and accordingly, at any instant in time, an asynchronously cycling population would be expected have 45% of its cells in the G1 Phase, 32% in the S Phase, 18% in the G2 Phase and 5% in the M Phase. FIG. 3 shows a representative phase distribution diagram for cells having a 24 hour cycle time, as well as the approximate location of known checkpoints.

Figure 4:
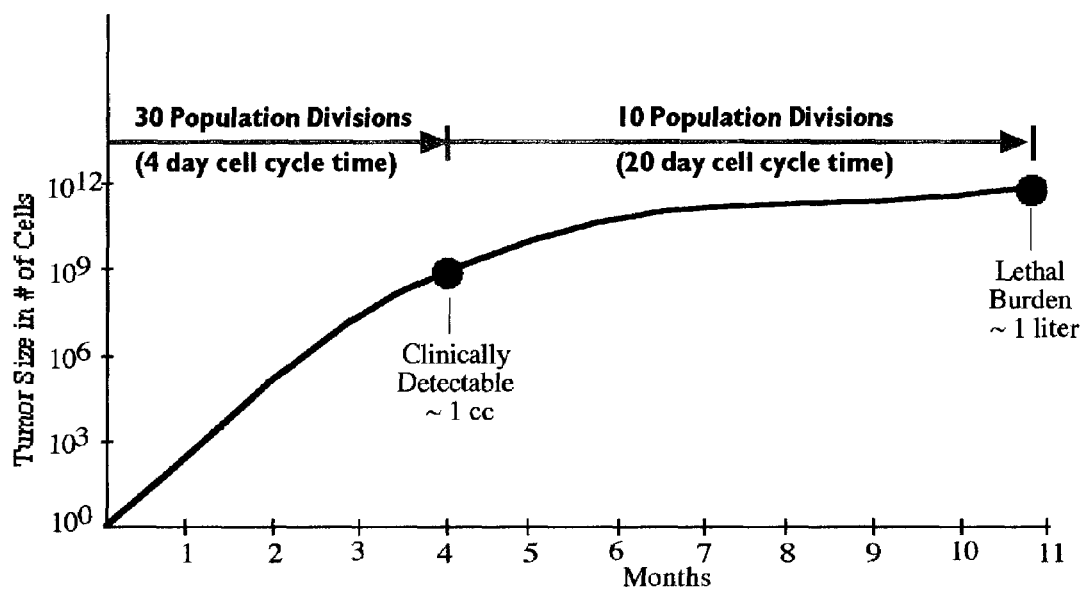
FIG. 4 shows the Gompertzian growth profile for a representative cancer.

Mathematically, from the single initial cancer cell it takes 30 population cell divisions (i.e. from 1 cell to 2, 4, 8, 16, etc. . . . ) for the tumor to reach a clinically detectable mass of 1 billion cells or ~1 cc and only 10 more population cell divisions after that to reach lethal burden at 1 trillion cells or ~1 liter. However, the rate of cancer's growth is not uniform. Cancer growth follows what is known as a Gompertzian growth curve (Harrison's, 15th ed. p. 530). A tumor grows about 5 times faster up to the 1 billion cell mass than it does from the 1 billion cell mass to the 1 trillion cell mass. Internal pressure from the crowding tumor mass eventually restricts blood flow and alters other cellular mechanisms, resulting in a slowing down of the tumor growth rate. FIG. 4 shows the Gompertzian Growth curve for a representative cancer cell with a genetic mutation profile that is "hard wired" to divide once every 4 days, an which will eventually crowd itself becoming nutrient or otherwise limited to dividing once every ~20 days as it moves past the 1 billion cell mass, which leaves ~7 months before it reaches lethal burden in the absence of intervention.

As disclosed by applicant in application Ser. No. 09/991,427, when chemotherapy is administered, it wipes out part of the tumor, relieving pressure and restoring blood flow to at least some parts of the tumor. A portion of the surviving cancer cells will resume the 4 day division time until they recrowd and once again restrict their own growth rate. Mathematically, this is a catastrophic event in the context of the phase specific regimen as the accelerated cancer cells are now phase asynchronous to the regimen—they are no longer in the queue were they were supposed to be in order to be killed by the next administration of phase specific chemo. A 4 day cycle time implies an ~1.3 day S-Phase time meaning that daily administrations of chemo would be required (i.e. so that no cells slipped past the S-Phase before the next administration of the S-Phase chemotherapeutic). In a 7 day administration interval, entire sub populations would accelerate through the S-Phase before the next hit of chemo, resulting in failure to achieve curative result.

In context of Gompertzian acceleration, a 7 day S-Phase specific regimen could only be curative in an extremely small percentage of cancers (i.e. 1) exceptionally weak mutation profiles "hard wired" at a 21+ day cycle rate and 2) some subset of the approximately 10% of cancers that do not posses the telomerase mutation and are close to the senescence point). In context of Gompertzian acceleration, a 7 day regimen would mathematically only increase life expectancy over best supportive care (BSC) by killing back 32% of the cancer cell population each administration, resulting in delaying the progression to lethal burden. To corroborate the purely palliative prognosis under prior art, in application Ser. No. 09/991,427 p. 11-12, applicant computed the mathematically projected survival time for two clinical trials using 7 day, S-Phase chemotherapeutic regimens for colon cancer, assuming that Gompertzian acceleration occurred, causing phase asynchronicity of the cancer cells to subsequent administrations of the phase specific chemotherapeutic. The actual median survival of both clinical trials was within the week projected under the mathematical calculation, corroborating Gompertzian related curative failure.

Preface to Examples—Cell Cycle Times and Cancer

The cell cycle time of normal rapidly proliferating cells (e.g. bone marrow, gastrointestinal stem cells, hair, and skin) is between 19 to 25 hours. Epithelial cells that line the lumen of the gut have an even shorter cell cycle time of approximately 11 hours.

A tumor's cell cycle time (above the 1 cc mass) is much longer by contrast. The colon cancer median survival of 6.5 months with only best supportive care (BSC) (PDR p. 2414) implies an approximately 19 day colon cancer cell cycle time (i.e. 6.5 mo.=195 days & ~10 cell cycles required from the first clinically detectable tumor of 1 bil. cells to lethal burden at 1 tril. cells=~19 days per cell cycle). Lung cancer has around the same cell cycle time (HPIM 14th ed. p. 559) with NSCLC survival of 8.5 months for asymptomatic patients and 6 months for symptomatic patients.

Figure 5:
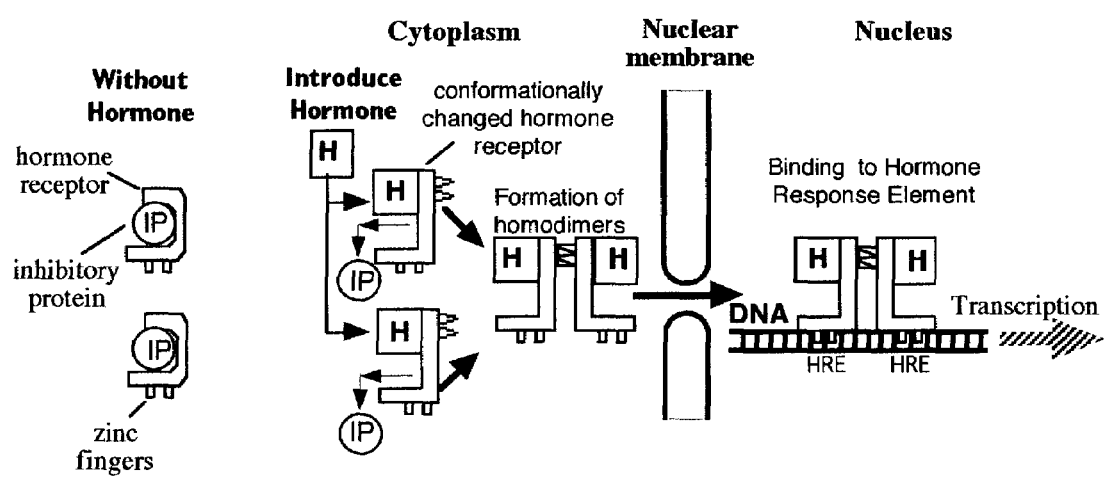
FIG. 5 shows the endocrine/endocrine receptor interactions.

Endocrine dependent tumors have an even longer cell cycle time, in the ballpark of ~30 days, as disclosed in application Ser. No. 09/991,427. The longer cycle time is related to endocrine hormone binding to specialized nuclear receptors (an additional growth pathway), required to drive the tumor throughout the cell cycle. FIG. 5 shows a schematized diagram of the endocrine/endocrine receptor interaction. Endocrine receptors are not expressed on the cell surface like growth factor receptors, but are intracellular and migrate into the nucleus when activated by endocrine binding. Endocrine hormones such as estrogen increase the transcription rate of proteins and peptides involved in growth control and DNA replication (BP p. 94). Because of indigenous oscillations in hormone levels during the menstrual cycle, the resulting hormone dependent distortion of cell cycle times as well as S-Phase duration distortion adds another layer of synchronization complexity in addition to Gompertzian acceleration.

Reduction to Practice—Distinction From Prior Art and Definitions

Due in part to the novel methods of present invention it is necessary to make several important distinctions in definitions between present invention and prior art as well as define novel methods for computing appropriate administration intervals for use with phase specific chemotherapeutics.

The prior art concept of "maximum tolerated dose" is not used in present invention. There is no rational basis for using a "maximum tolerated dose" as mathematically it contributes nothing to curative result and only contributes to excessive systemic toxicity. Present invention favors the lowest dose that will induce a desired kill rate in the phase (i.e. 100% S-Phase kill rate) and has the shortest in vivo efficacy time (i.e. shortest terminal half life), hereinafter referred to as the "shortest efficacious dose". As an example, under prior art, the S-Phase chemotherapeutic Camptosar® comes in two administration regimens, 340 mg/m2 which is administered once every 3 weeks and 125 mg/m2 which is administered once every week. The terminal half lives of the doses are 21.0 and 10.4 hours, respectively. The terminal half lives are important in systemic toxicity. Prior art's high dose (HD) regimen of 340 mg has a 21 hour terminal half life, which is close to the hematologic cell cycle time (~24 hours), which means that ~90+% of hemopoietic cells and >99% of gastrointestinal epithelial cells (~11 hour cell cycle time) will also be killed as they pass through the S-Phase during the chemotherapeutic's efficacy period. In the same time period about 32% of a 20 day tumor's cells will be in the S-Phase and be killed. Likewise, prior art's low dose (LD) of 125 mg/m2 has a 10.4 hour terminal half life, implying slightly less than half of hemopoietic cells will die and roughly 95% of gastrointestinal epithelial cells will die in order to achieve a 32% tumor kill rate. In contrast, an example of an ideal "shortest efficacious dose" under present invention would achieve the 100% S-Phase kill rate and have a terminal half life of an hour or two. The resulting systemic cell kill rate and tumor kill rate would both be approximately 32%, achieving the same tumor kill rate as under prior art but at a fraction of the systemic toxicity. For each additional hour the chemotherapeutic remains active in the blood approximately 4% (1 hour÷24 hours) of the bone marrow cells will enter the S-Phase increasing the hematologic toxicity from 32% to 36% to 40% etc. . . . for each additional hour of terminal half life. A terminal half life of 5 hours will kill just under half of bone marrow cells, which should allow the population to fully replenish itself within 48 hours (i.e. 4.4 hours for leading edge of unviable cells to reach G2 checkpoint and be eliminated plus 8 hours to assemble cell cycle control system in response to population density regulation plus 24 hour cell cycle=36.4 hours for leading edge and similarly 44 hours for trailing edge).

Prior art's "combination chemotherapy" is also defined differently. Present invention makes a critical distinction between "cytotoxic" and "cytostatic" chemotherapeutic agents. Cytostatic agents are defined as substances that induce cellular arrest or slow down the cell cycle. Cytotoxic agents kill cells or lethally damage cells so they are killed or subsequently removed at checkpoints. Prior art uses both cytotoxic and cytostatic agents as part of combination chemotherapeutic regimens. It will be shown how cytostatic agents, as used under prior art, cancel out the effects of phase specific chemotherapeutics. In contrast, present invention uses cytostatic drugs as conforming agents, in a manner that does not cancel out the benefits of the cytotoxic chemotherapy, and in a manner that prevents Gompertzian acceleration, so as to provide curative result.

Prior art uses fixed administration intervals (AIs) based on some calendar schedule (e.g. daily, weekly). Present invention computes AIs based on physiological events. Although the timeline of the physiological events can be mathematically approximated, present invention uses the mathematical approximations to schedule PET scans to more precisely adjust for possible deviations based on factors such as different cancer mutation profiles, differing drug metabolism rates among individuals, etc. . . . and accordingly more precisely keep the cancer cells and phase specific chemotherapeutic administrations synchronized.

Present invention uses a "mid point rule" for scheduling administrations. By this it is meant that administrations of phase specific chemotherapeutics are given frequently enough so that no cell gets more than half way through the susceptible phase before an administration of chemotherapeutic.

Chemotherapeutic or cytotoxic regimen as used in this application is defined as a regimen that does not leave a single surviving cancer cell at its conclusion. Conforming Regimen as defined in present invention leaves cancer cells in a position were they will all cycle at the same rate.

The word "cycle" is used in this application with two different meanings; i.e. as "cell cycle" or as "chemotherapeutic administration cycle" and needs to be interpreted in context.

Cytostatic Agent Example

Herceptin® clinical trials are of interest to present invention as they will allow applicant to demonstrate how to use cytostatic agents to prevent phase asynchronicity and chemotherapeutic failure. A summary of the Phase III clinical trials conducted on 469 patients with HER2 overexpression driven breast cancer is contained in the enclosed Herceptin® Full Prescribing Information.

HER2 is a human epidermal growth f EGF receptor of the type depicted in FIG. 1. Growth factors are continually produced as part of population density maintenance and neighboring cells continually compete for growth factors (MBOC 898). This can also be inferred from FIG. 2a as the G1 Cyclin D/CDK 4/6 complexes (mitogen driven) are always present at some level, indicating extracellular mitogens are also continually present. An overexpression of growth factor receptors allows the over expressing cells to preferentially take up more growth factors. Intracellularly, this is indistinguishable from a elevated amount of ambient growth factors being present. The result is the cell is induced into initiating a cell cycle.

Mathematically, a cancer driven in this way is highly predictable in that it most closely resembles a normal actively cycling cell. All three major pathways shown in FIG. 1 are triggered at the highest level, in a manner identical to that under normal mitogen driven control. Accordingly, the proportion of time spent in each phase should mirror that of normal actively cycling cells, allowing for fairly precise mathematical projections. Likewise, inhibiting expression or functionality of the receptor would result in effects that are understood and predictable, as they would be analogous to growth factor deprivation. Growth factor deprivation dismantles the cell cycle control system, causing cellular arrest in cells that have not yet reached the G1 checkpoint (see FIG. 2a, mitogen dependent portion of chart). Cells past the G1 checkpoint will continue through the cell cycle and arrest as they enter G1, entering what is referred to as a G0 or no growth state (MBOC 896-897).

The multi center, randomized, controlled clinical trial was conducted on patients with metastatic breast cancer expressing HER2 receptors, who had not been previously treated with chemotherapy. Patients were randomized to receive chemotherapy alone or in combination with Herceptin® given intravenously as a 4 mg/kg loading dose followed by weekly doses of 2 mg/kg. The chemotherapy consisted of either Paclitaxel at 175 mg/m2 over 3 hours every 21 days for 6 cycles or a combination of Anthracycline (A) plus Cyclophosphamide (C) every 21 days for 6 cycles. The 6 cycles implies a 99% kill rate under prior art's Skipper log cell kill model. Paclitaxel is a M-Phase specific cytotoxic, Anthracycline is a S-Phase specific cytotoxic, and Cyclophosphamide is a non-phase specific specific cytotoxic. Herceptin is a cytostatic agent—it is a monoclonal antibody that binds with high affinity to the extracellular domain of the HER2 receptor, preventing it from binding with ambient mitogens.

The numbers used below in mathematical calculations have been rounded for convenience. A month is assumed to have 30 days. The tumor kill rate used is 100% of cells in a phase for phase specific chemotherapeutics. Terminal half life numbers, where cited, were obtained from the Physicians Desk Reference (PDR). If terminal half lives were not available, but half lives were, the terminal half life was computed using the midpoint of 3.5 half lives=terminal half life (HPIM 15th ed., p. 420: for practical purposes, a first order elimination process reaches completion after 3 to 4 half lives). The 6 cycles of 21 days per cycle has been rounded to 4 months for the regimen duration time (i.e. 6×21 days=126 days÷30 day/mo-~=4 months). Since breast cancer is typically an endocrine dependent cancer (~two thirds of breast cancers are estrogen receptor positive and 40%-50% are progesterone receptor positive) the 30 day cell cycle time is used. Because of the long 21 day administration intervals combined with no measures taken to prevent Gompertzian acceleration, the 30 day cycle rate should be fairly accurate as the acceleration in growth would fairly quickly crowd out the empty spaces created by the chemotherapeutic and return the growth rate back to the slower 30 day rate used in calculations.

Mathematically, the 21 day intervals used in the trials can never be expected to remain synchronized with the susceptible phase. S-Phase duration at the 30 day cell cycle rate would last only 9.6 days (i.e. 30 day cycle×32% of time spent in S-Phase=9.6 days spent in S-Phase). The Gompertzian accelerated rate of 6 days cell cycle time and 2 days in S-Phase is moot as the administration intervals are too long even without the occurrence of Gompertzian acceleration. The 21 day intervals used under prior art can effectively only yield an extension in life expectancy from periodically setting back the cancer population's progression to lethal burden. That extension in life expectancy can be mathematically calculated (projected) in order to corroborate the validity of the underlying mechanisms of action as described by applicant as well as establish the efficacy level of the cytostatic agent.

Individually, a cytostatic, such as Herceptin, administered over 4 months would be expected to extend life expectancy by ~4 months, the amount of the cellular arrest time. Individually, an S-Phase cytotoxic administered asynchronously as in the trials would wipe out 32% of the tumor each time it was administered, times 6 administrations equals ~2 population division cycles (i.e. 6×0.32) and since a population division cycle equals 30 days, the increase in life expectancy would be 2 months. Individually, an M-Phase cytotoxic's contribution would be 6×0.05=0.3 months. A summary of the median life expectancy observed is presented below in TABLE 1:

TABLE 1

Observed Median Survival Data (in months)

|  | Herceptin + Paclitaxel | Paclitaxel | Herceptin + AC | AC |
|---|---|---|---|---|
| Median Survival | 22.1 | 18.4 | 26.8 | 21.4 |
| Increase w/Herceptin | 3.7 |  | 5.4 |  |

A "best supportive care" (BSC) life expectancy can be computed most accurately from the M-Phase single agent trial as its individual contribution is only projected to be 0.3 months. Thus the BSC would be around 18.1 months (18.4-0.3) and since the study was randomized it can be used as a baseline across the other arms.

Because prior art combination chemotherapy does not distinguish between cytostatic and cytotoxic agents, the cumulative benefit cannot be obtained by adding the individual contributions, as the cytostatic agent negates a large part of the benefit derived from phase specific chemotherapeutics.

TABLE 2 shows the mathematically projected survival times under the 4 arms as compared to the actually observed survival rates. It is constructed starting with the 18.1 BSC baseline and adding the projected increase in survival from each regimen. The individual Paclitaxel regimen was used in computing the BSC so it would be equal to the observed by definition.

TABLE 2

Projected Survival (in months)

|  | Herceptin + Paclitaxel | Paclitaxel | Herceptin + AC | AC |
|---|---|---|---|---|
| BSC (Computed) | 18.1 | 18.1 | 18.1 | 18.1 |
| Projected Survival over BSC | 4.0 | .3 | 8.1 |  |
| Projected Median Survival | 22.1 | 18.4 | 26.2 |  |
| Actual Median Survival | 22.1 | 18.4 | 26.8 | 21.4 |

Herceptin+Paclitaxel are projected to increase life expectancy 4 months. The benefit is basically only related to Herceptin's 4 month individual extension of life expectancy. The only benefit of Paclitaxel (M-Phase specific) would come from the first administration, where the 5% tumor reduction would translate into a insignificant 0.05 month added to life expectancy. This is because a cytostatic agent such as Herceptin would induce cellular arrest, with the roughly two thirds of cells past the G1 checkpoint being swept through the cell cycle and into G0 within 20 days and the other one third of cells arrested at the G1 checkpoint. By the time the next administration of Paclitaxel was given in 21 days, there would no longer be any cells in the M-Phase and the tumor kill rate would be zero for Paclitaxel administrations 2,3,4,5, and 6. Systemic toxicity from the Paclitaxel however would remain unchanged. The 175 mg/m2 Paclitaxel dose has a terminal half life of 20.2 hours and is infused over a 3 hour period, putting it in the blood for about 23 hours. Since bone marrow cells are on a 24 hour clock, roughly 96% of them would pass through the M-Phase in that time period and be killed. This also tends to support the unobviousness of present invention over prior art, as if it were obvious, no rational person would administer a drug that caused massive systemic toxicity with zero therapeutic benefit, 5 times.

The administrations of Anthracycline (S-Phase cytotoxic) and Cyclophosphamide (non-phase specific but cell cycle active) combine a known projected benefit and an unknown benefit, respectively. The AC arm of the trial will be used to compute the unknown benefit from the non-phase specific cytotoxic which can then be used to project the increased life expectancy under the Herceptin+AC arm.

The 21.4 median survival time of the AC arm is 3.3 months longer than the BSC baseline of 18.1 months. The 3.3 months=3.3 population cycles killed back over 6 administrations for a tumor population kill rate of 55% per administration (i.e. 3.3÷6). Since the S-Phase cytotoxic's kill rate is 32%, the additional 23% (i.e. 55%-32%) kill rate in the 68% of cells not in the S-Phase cells represents a 34% (23%÷68%) inherent tumor kill rate for the non specific chemotherapeutic. The inherent kill rate of 34% represents the individual contribution the non phase specific would make on its own, if the S-Phase cytotoxic had not been administered, masking part of the non phase specific kill rate related to cells in the S-Phase. In combination, since there is an overlap in cell killing in the S-Phase, the cumulative AC kill rate is 55% (versus the 32%+34%=66% sum of the individual kill rates). Having identified the unknown non phase specific kill rate as 34%, we can now project the expected increase in life expectancy from the Herceptin+AC arm.

The first administration of Herceptin+AC would kill back the tumor by 55% leaving 45% survivors. Herceptin would put the tumor in cellular arrest for the next 4 months, as previously disclosed in the Herceptin+Paclitaxel projection. Likewise, the next 5 administrations of the S-Phase specific chemotherapeutic would provide 0 tumor kill rate as the tumor cells would all be arrested in the G Phase. Cyclophosphamide, on the other hand, is an alkylating agent, and alkylation of DNA can occur at any phase of the cell cycle. DNA damage would continue to accumulate with successive administrations, however actual cell death from the accumulated damage would not occur until the cells resumed cycling and encountered genotoxic checkpoints, at which time the doomed cells would be removed apoptotically by P53 dependent and independent pathways. Successive administrations are mathematically projected at inflicting 34% mortal damage to "surviving cells" (according to log cell kill methodology outline in HPIM 14th ed. p. 528), where surviving cells are meant to be cells that have not yet accumulated enough genetic damage to die when cycling is resumed and genotoxic checkpoints are encountered. These are shown in TABLE 3 below:

TABLE 3

Log Cell Kill Model for Herceptin + AC

| Cycle | Functional Chemo(s) | Kill % | Survivors |
|---|---|---|---|
|  |  |  | 100.0 |
| 1 | AC | 55% | 45.0 |
| 2 | C | 34% | 29.7 |
| 3 | C | 34% | 19.6 |
| 4 | C | 34% | 12.9 |
| 5 | C | 34% | 8.5 |
| 6 | C | 34% | 5.6 |

The 5.6% "survivable cells" at the end of the regimen would take 4.12 population cycles to get back to 100% (i.e. 5.6 to 11.2, 22.4, 44.8, 89.6, 179). Thus, the addition in life expectancy from the chemotherapy would be 4.1 months plus 4 months from Herceptin's cellular arrest for a total of 8.1 months over the BSC survival time, or 26.2 survival time versus the 26.8 observed.

Novelty and Unobviousness over Prior Art:

The projected survival of 22.1 months versus the observed 22.1 for the Herceptin+Paclitaxel regimen and the projected survival of 26.2 months versus the observed 26.8 for the Herceptin+AC regimen not only corroborates the validity of the underlying mechanisms of action but shows that Herceptin is very effective at inducing cellular arrest. It also shows that prior art regimens can only be projected to increase survival time (palliative) but can not yield curative result. It is the primary object of present invention to provide regimens that yield curative result.

Prior art does not distinguish between cytotoxic and cytostatic agents and consequently uses them antagonistically in combination chemotherapeutic regimens. Present invention will disclose how to use them synergistically.

Prior art makes no attempt to synchronize phase specific chemotherapeutics to the susceptible phase in the cancer cell population, thus allowing them to slip past the susceptible phase before the next chemotherapeutic administration, and preventing the possibility of curative result. Present invention will solve this problem, in reverse, by synchronizing the cancer cells to a phase specific chemotherapeutic through the use of cancer specific cytostatic agents.

Reduction to Practice Examples

Present invention's "cancer cell cycle time conforming regimen" or "Conforming Regimen" uses cytostatic agents in conjunction with cytotoxic agents to reduce larger tumors and preserve the size reduction so that all cancer cells will posses the same (i.e. fastest possible) cell cycle time in response to a subsequent chemotherapeutic regimen. Thus, Gompertzian acceleration related asynchronicity are avoided as all cancer cells are by definition at the most accelerated rate, and a chemotherapeutic regimen using AIs for the fastest rate is then employed.

The second method termed "Phase Compressed Chemotherapy" relates to use of agents in conjunction with cytotoxic agents in a manner that, with each successive administration cycle, progressively narrows the surviving cancer cells into a tight(er) band in a phase of the cell cycle, reducing the number of cytotoxic administrations required versus prior art and increasing the probability of curative outcome over prior art.

EXAMPLE 1

Single Tumor

A patient presents with a 2 cc inoperable tumor in the lung. It is determined the cancer has a 3+ level of HER2 overexpression as measured by prior art immunohistochemical assessment methods.

The cancer cells are determined to have a 4 day cell cycle rate below the 1 cc level and 20 days above the 1 cc level (e.g. a biopsy of the cancer cells cultured in vitro reveals the 4 day cycle, MRI, CAT, PET or other imaging method taken some time apart reveal increase in tumor size corresponding to a 20 day rate, or any other suitable method of determining cell cycle time may be substituted.)

Under prior art, an S-Phase cytotoxic would cause genotoxic damage to cells in the S-Phase, and as the reach the G2 checkpoint they are removed. The surviving cells find themselves in a much more favorable environment and accelerate their growth up to 5 times faster (i.e. 4 day cycle) until they recrowd and are once again nutrient limited to a 20 day cycle according to the Gompertzian growth curve. Using the midpoint rule previously defined, a single cycle under the Skipper log cell kill model, for a 20 day cycling cell and for a 4 day cycling cell are shown in TABLE 4:

TABLE 4

Conventional S-Phase Chemotherapy Cycle at Midpoint

|  | 20 day cycle | 4 day cycle |
| --- | --- | --- |
| S-Phase Duration | 6 days | 1.3 days |
| S Chemo Admin. on Days (to = 1 cycle) | 1, 3, 6, 9, 12, 15, 18, 21 | 1, 2, 3, 4, 5 |

Figure 6A:
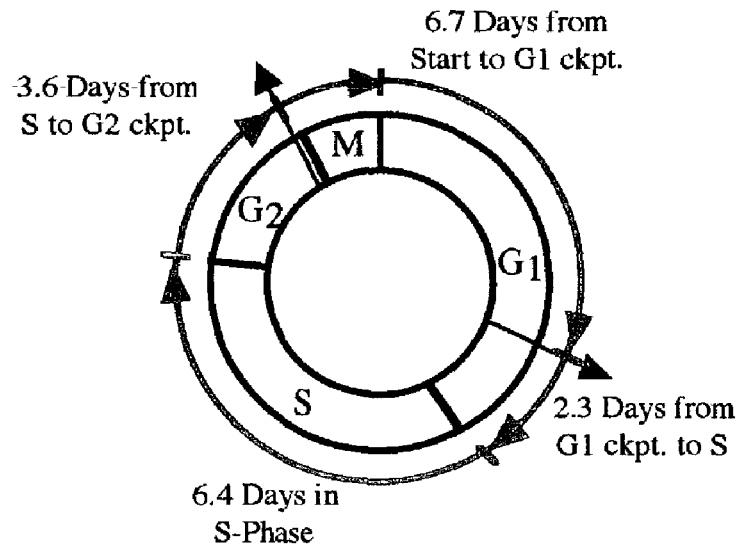
FIGS. 6a and 6b show the phase distribution for the representative 20 day and 4 day tumor cell cycle rate, respectively.
Figure 6B:
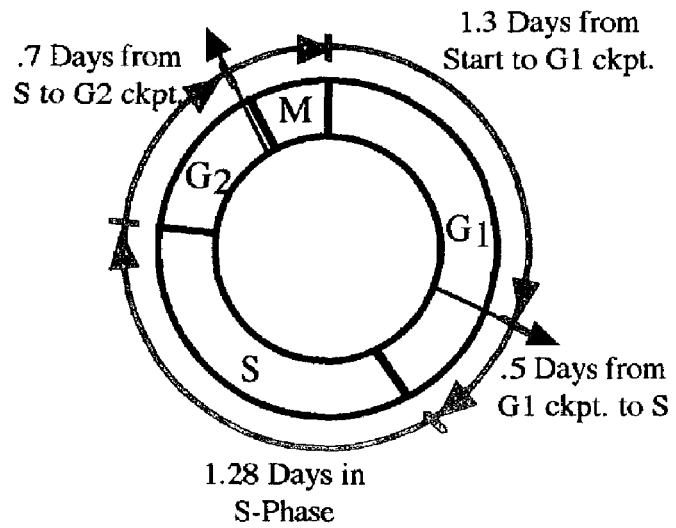

Conforming Regimen for Example 1:

Under present invention the patient is first put on a Conforming Regimen. FIG. 6a and FIG. 6b are provided for reference and show the phase distribution and duration diagrams for a representative, non endocrine dependent, 20 and 4 day cycling cancer cell, respectively.

On day 0 and day 6, a high S-Phase kill rate cytotoxic chemo (e.g. 100 mg/m2 of irinotecan, 150 mg/m2 etoposide, or other suitable S-Phase chemotherapeutic) is administered. On day 3.5, a intravenous infusion loading dose of 4 mg/kg of the cytostatic agent Trastuzumab is administered followed by a 2 mg/kg maintenance dose in one week.

Sweep 1 in FIGS. 7a-7d diagrammatically shows the progression of the 20 day cancer cells throughout the Conforming Regimen.

Figure 7A:
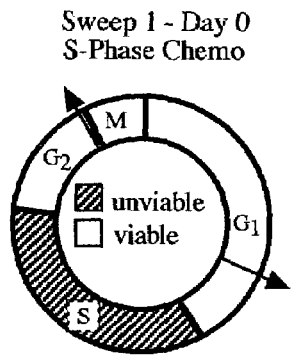
FIGS. 7a-7d diagrammatically show the cancer cell population phase distribution for a single tumor, at selected points during a Conforming Regimen

FIG. 7a shows a homogenous distribution of cells throughout the cell cycle and the hatched area shows the roughly 32% of cells rendered unviable by the first administration of the cytotoxic chemotherapeutic on Day 0. The leading edge of the unviable cells will approach the G2 checkpoint in approximately 3.6 days (see FIG. 6a) where they will be sequentially removed via P53 dependent and independent pathways as they pass the checkpoint.

Figure 7B:
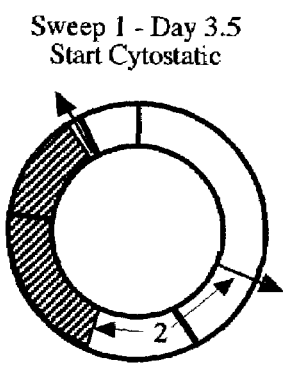

FIG. 7b shows the position of the unviable cells when the cytostatic agent is administered on day 3.5. Behind the trailing edge of the unviable cells there are 3.5 days worth of viable cells that have entered the S-Phase and 2.3 days of viable cells between the G1 checkpoint and the S-Phase, for a total of 5.8 days of cells and labeled as "2" in FIG. 7b. The administration of the cytostatic Trastuzumab causes cellular arrest at the G1 checkpoint for cells in the G-Phase that have not yet reached the checkpoint and all other cells will continue through the cell cycle where they will arrest in the G0 state after mitosis.

Figure 7C:
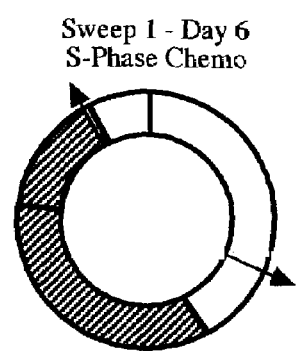

FIG. 7c shows the administration of the S-Phase Cytotoxic on day 6. The cells previously marked as "2" in FIG. 7b have all entered the S-Phase by day 6 and are rendered unviable by the second hit of the S-Phase Cytotoxic. The mid point rule is not necessary in a conforming regimen as it is not necessary to insure 100% of cells are killed, as in a chemotherapeutic regimen.

Figure 7D:
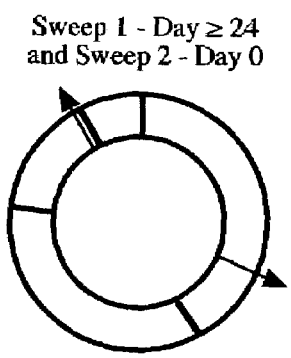

After the unviable cells have been removed, any survivors would be aggregated between the start of the G phase and the G1 checkpoint as shown in FIG. 7d. FIG. 7d thus represents the end point of the Conforming Regimen, whereby 61% of the tumor has been killed (i.e. (6.4 days+5.8 days)÷20 day total cycle) reducing it to a 0.78 cc mass, the surviving cells have been aggregated into a part of a single phase, where they are held arrested until the start of chemotherapy. FIG. 7d is therefore also used as the start point for a chemotherapeutic regimen, and it is a start point were all cancer cells have been "conformed" to the same cycle rate of 4 days upon exit from arrest. The cytostatic is conservatively administered to have an efficacy period greater than the time from the G1 checkpoint to the end of the M phase for the slowest possible cell cycle time (i.e. 13.3 days for a 20 day cycling cell). The mean half life of the Trastuzumab at the doses administered in the example is 5.8 days implying a terminal half life of around 20.3 days (i.e. 5.8×3.5) after the last administration, implying the surviving cancer cells would resume cycling around day 27 in the example above. Preferred embodiment favors daily PET scans using a glucose tracer, starting several days before the expected resumption of cycling, to more precisely identify when the cells have started cycling again, however, other measures of monitoring metabolic activity, thermal imaging, or any other suitable methods may be substituted. Resumption of cycling indicates the start point for the chemotherapeutic regimen.

Utility Over Prior Art:

Without a Conforming Regimen, conventional prior art chemotherapeutic regimens can not yield curative result in the example above. HPIM 15th ed. Table 84-2 p. 538-541, enclosed under the IDS, provides a good summary of prior art chemotherapeutic regimens. S-Phase specific regimens that use daily administrations of from 3-8 consecutive days are common under prior art, and can remain synchronous to a 4 day cycling tumor, however a 2 cc tumor is on a 20 day cycle, with periodic localized bursts of up to 4 day cycling time for vacancies created by removal of unviable cells at appropriate checkpoints. Since the unviable cells will not start reaching the G2 checkpoint for almost 4 days in a 20 day cycling cell (see FIG. 6a), 4 consecutive daily administrations can kill, at most, the 32% of cells in the S-Phase when administrations started plus the roughly 20% of new cells that entered the S-Phase in the next 4 days (i.e. 4+20) for a total tumor kill rate of 52% (i.e. 32%+20%) per cycle, requiring 30 cycles per the Skipper log cell kill model with no regrowth in between cycles. In the best case scenario of daily S-Phase cytotoxic administrations for 8 consecutive days, 32% of cells in the S-Phase at start of administration would be rendered unviable plus, 40% of new cells will enter the S-Phase over the next 8 days for a total of 72% of the original tumor population. Additionally, some cells in the tumor will be accelerated to a 4 day rate starting at around day 4, increasing the number of S-Phase entrants and tumor kill rate. Assuming a cell directly next to the tip of a capillary is removed, and it is surrounded by 5 cells (i.e. square configuration with on side bounded by blood vessel) accelerating the 5 surrounding, asynchronously cycling, cells into a 4 day cycle, they would have to grow only 20% before recrowding, which translates into spending only one day at the 4 day rate, or a 25% (i.e. 1 day÷4 day cycle) phase shift forward. This in turn implies that of the 28% of cells not already rendered unviable, an additional 25% will be pulled into the S-Phase by the acceleration and rendered unviable for and additional tumor kill rate of 7% (i.e. 28% viable× 25% pulled into susceptible phase by acceleration) for a total tumor kill rate of around 79% (i.e. 72%+7%), which is also clearly not curative.

Administration intervals of 7 days and 21 days are also employed under prior art. A 20 day non endocrine tumor has a 6.3 day S-Phase, so even if the 7 day administration had long enough of a terminal half life to reach across the 0.7 day gap as well as being able to kill cells just about to exit the S-Phase, subsequent administrations could not kill the accelerated cells which are no longer synchronous to subsequent administrations in the administration cycle, thus preventing curative result. Applicant has no idea why anyone would use a 21 day administration interval if they desired a curative result.

The Conforming Regimen leaves all cells in a position where they will cycle at the same 4 day rate, not the 20 day rate, not something in between a 4 day rate and a 20 day rate, not at the 20 day rate for part of the time and the 4 day rate for some other part of the time, but for a single 4 day rate all of the time, which can be synchronously matched to appropriate successive administrations of a phase specific cytotoxic chemotherapeutic over an administration cycle.

Phase Compressing Chemotherapy for Example 1:

After the Conforming Regimen, prior art chemotherapy, geared for a 4 day cell cycle time may be employed. Since the S-Phase lasts only 1.3 days in a 4 day cell cycle, daily administrations are necessary for 5 consecutive days as shown above in TABLE 4 to constitute one administration cycle per the Skipper log cell kill model. Consecutive administration for 8 days as mentioned above would provide a better margin of error for non uniformities in resumption of cycling among cells.

The Skipper log cell kill model does not allow for tumor regrowth between administration cycles (hereinafter referred to as "inter-cycle regrowth") and accordingly prior art regimens will fail unless the cytotoxic has a 100% phase kill rate. Since 100% kill rates are not likely, prior art chemotherapeutic regimens are prone to inter-cycle regrowth related failures, in addition to Gompertzian acceleration related failures.

Present invention proposes a novel "Phase Compressing Chemotherapeutic Regimen" which prevents both inter-cycle regrowth and Gompertzian acceleration related failures as well as increasing curative probabilities and reducing the number of cytotoxic administrations required to achieve curative result under the Skipper log cell kill model. The Phase Compressing Regimen is a chemotherapeutic regimen, which means not a single cell can be allowed to survive. The Phase Compressing Regimen is done in "sweeps" or "rounds" where the first sweep further compresses the cells into a narrow band while also being cytotoxic, and all subsequent sweeps re-compress any surviving cells into the narrow band while also being cytotoxic.

An example of a Phase Compressing Regimen, where Day 0 is when the cells resumed cycling after the Conforming Regimen, would be: First Sweep—on Day 1 and 2a 99+% S-Phase kill rate chemotherapeutic is administered (e.g. 150 mg./m2 etoposide, etc. . . . ) and the cytostatic trastuzumab is administered on day 2 (e.g. 2 mg/kg dose, or any other suitable dose). Second and all subsequent sweeps—where Day 0 is when the cells have resumed cycling from the prior sweep, on Day 2.5 a 99+% S-Phase chemotherapeutic is administered (e.g. 100 mg/m2 of irinotecan, 150 mg/m2 etoposide, etc. . . . ) and the cytostatic is also administered on day 2.5 (e.g. 2 mg/kg dose, or any other suitable dose). The regimen consists of 5 consecutive sweeps.

Figure 7E:
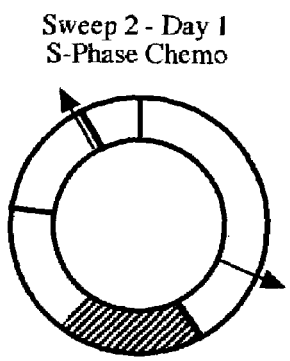
Figure 7F:
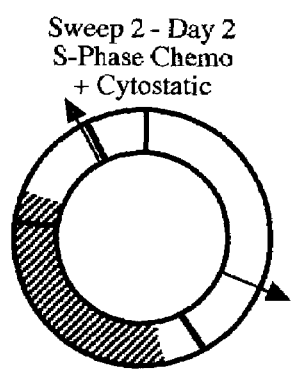
Figure 7G:
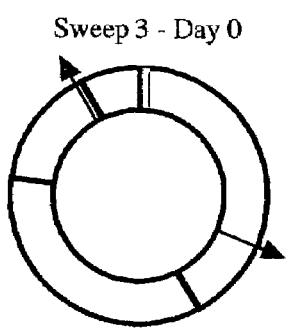
Figure 7H:
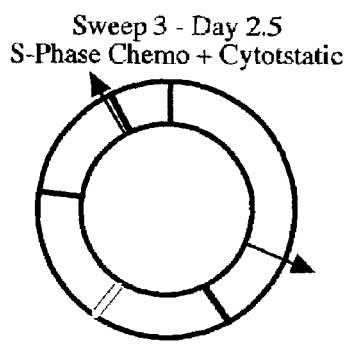
Figure 7I:
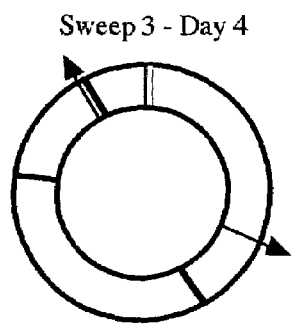

The first sweep is depicted diagrammatically in FIGS. 7d to 7f and all subsequent sweeps are depicted in FIGS. 7g-7i.

First Sweep: FIG. 7d shows Day 0, the day the cells resume cycling. FIG. 6b shows that it would take about 1.1 days for the leading edge of the "4 day conformed" cells to get from the G1 checkpoint to the midpoint of the S-Phase, and as depicted in FIG. 7e, at which time the first dose of the S-Phase cytotoxic is administered. FIG. 7e shows the cancer cell made unviable by this dose. The trailing edge of cells will enter the S-Phase in 1.8 days. FIG. 7f shows the cells on Day 2 when the second administration of the cytotoxic is administered together with the first administration of the cytostatic. The remaining cells are rendered unviable by the cytotoxic and the cytostatic serves to halt any potential survivors as they enter the G phase.

Second and all Subsequent Sweeps: The second (an all subsequent) sweeps of Phase Compressing Chemotherapy are shown in FIG. 7g-7i. FIG. 7g shows the distribution of any surviving cells after a sweep of Phase Compressing Chemotherapy. After resumption of cycling (as confirmed by PET or other methods previously described) it takes the cells 2.44 days (i.e. 1.3+0.5+(1.28÷2) from FIG. 6b) to reach the midpoint of the S-Phase, at which time the single administration of S-Phase cytotoxic kills any possible survivors from the prior cycle and the cytostatic once again aggregates any potential survivors at the G phase entry point.

Subsequent sweeps or rounds of the Phase Compressing Chemotherapy repeat FIGS. 7g-7i, and are repeated no fewer times than indicated under the Skipper log cell kill model.

Utility over Prior Art:

The advantage of the Phase Compressing Regimen is that it greatly reduces the number of cytotoxic administrations required as well as greatly increases the probability of curative result over prior art. Under prior art, using a 99% S-Phase kill rate cytotoxic, a 1 billion cell tumor, 5 administrations to cover one sweep of all cells through the S-Phase as per TABLE 4, and 5 cycles required for the regimen under the Skipper log cell kill model to get the tumor below the one surviving cell number (i.e. $1,000,000,000 \times 0.01 \times 0.01 \times 0.01 \times 0.01 \times 0.01 = 0.1$) then a total of 25 cytotoxic administrations would be required for the prior art regimen (i.e. 5 admins./cycle times 5 cycles per regimen). Present invention's Phase Compressing Regimen requires 2 cytotoxic administrations for the first sweep, and only one cytotoxic administration for all subsequent sweeps. A comparable 5 sweeps under present invention uses only 6 administrations of cytotoxic chemotherapy versus 25 under prior art, to get to the 0.1 surviving cell number. Since the probabilities are cumulative, 10 cytotoxic administrations (i.e. 9 sweeps) under present invention's Phase Compressing Regimen would yield $1,000,000,000 \times 0.01 \times 0.01 \times 0.01 \times 0.01 \times 0.01 \times 0.01 \times 0.01 \times 0.01 \times 0.01 = 0.000000001$ surviving cell versus prior art's 25 administrations to get to 0.1 surviving cell.

Present invention's phase compressing regimen can also be designed to be a fraction of the time of prior art regimens. As an example, a 10 mg. dose of trastuzumab has a half life of 1.7 days, or terminal half life of 6 days (i.e. 1.7×3.5). Substituting the 10 mg. dose in the example, and assuming cytostatic efficacy at that dose, would yield a sweep duration of 8.5 days, and a full regimen duration of under 6 weeks (i.e. 8.5 days×5 sweeps) versus prior art regimens that last around 4 months.

EXAMPLE 2

Multiple Tumors

Several months after surgical removal of an 8 cc lung cancer mass, the patient presents with metastatic lung cancer, with a 2 cc tumor in the lung, a 1 cc tumor in the liver, a 0.5 cc tumor in the kidney and it is suspected there are one or more undetected metastatic sites where the tumor is too small to be detected yet. It is determined the cancer has a 3+ level of HER2 overexpression as measured by prior art immunohistochemical assessment methods.

The cancer cells are determined to have a 4 day cell cycle rate below the 1 cc level and 20 days above the 1 cc level (e.g. a biopsy of the cancer cells cultured in vitro reveals the 4 day cycle, MRI, CAT, PET or other imaging method taken some time apart reveal increase in tumor size corresponding to a 20 day rate for the larger tumors and/or 4 days for the small one, or any other suitable method of determining cell cycle time may be substituted.)

Conforming Regimen for Example 2:

Under present invention, On day 0, 3.5, day 6, a high S-Phase kill rate cytotoxic chemo (e.g. 150 mg/m2 etoposide, 50 mg/m2 of irinotecan, or other suitable S-Phase chemotherapeutic) is administered. On day 3.5, an intravenous infusion loading dose of 4 mg/kg of the cytostatic agent trastuzumab is administered followed by weekly doses of 2 mg/kg for 2 weeks.

Sweep 1 in FIGS. 8a-8d shows the results of the Conforming Regimen diagrammatically for the 2 cc tumor.

Figure 8A:
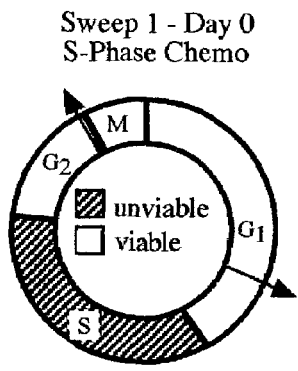
FIGS. 8a-8i show the cancer population phase distribution under a multiple tumor scenario for both the Conforming Regimen and for the Phase Compressing Regimen.

FIG. 8a shows a homogenous distribution of cells throughout the cell cycle and the hatched area shows the roughly 32% of cells rendered unviable by the first administration of the cytotoxic chemotherapeutic on Day 0. In the 2 cc tumor (20 day cell cycle time) the leading edge of the unviable cells will approach the G2 checkpoint in approximately 3.6 days (see FIG. 6a) where they will be sequentially removed via P53 dependent and independent pathways as they pass the checkpoint.

Figure 8B:
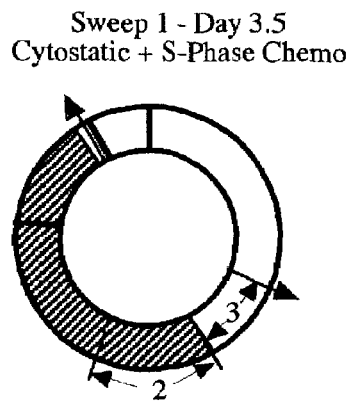

FIG. 8b shows the position of the unviable cells when the S-Phase cytotoxic and G-Phase cytostatic are administered on day 3.5. Behind the trailing edge of the unviable cells there are 3.5 days worth of new cells that have entered the S-Phase and are now made unviable (labeled "2" in FIG. 8b) by the second administration of the cytotoxic and 2.3 days of viable cells between the G1 checkpoint and the S-Phase (labeled "3" in FIG. 8b) which will be the target of the cytotoxic administration of Day 6, for a total of 5.8 days of cells.

Figure 8C:
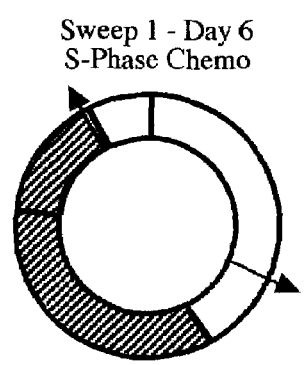

FIG. 8c shows the last of the cells ((labeled "3" in FIG. 8b) made unviable.

Figure 8D:
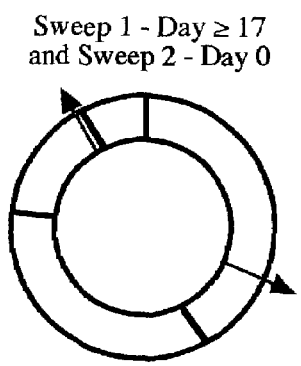

FIG. 8d shows the end point of the Conforming Regimen, whereby 61% of the 2 cc tumor has been killed (i.e. (6.4 days+5.8 days)÷20 day total cycle) reducing it to a 0.78 cc mass, the surviving cells have been aggregated into a part of a single phase, where they are held arrested until the start of chemotherapy.

The additional cytotoxic administration on Day 3.5 (versus the Conforming Regimen of Example 1) uses the midpoint rule for a more reliable kill rate. It also hits the 4 day cycling tumors one more time before they are swept into cellular arrest and thus keeps the <1 cc tumors further back from the 1 cc mark. The 1 cc tumor size is a transition point in growth rate change and neither the tumor size is necessarily exact (i.e. could be at the 0.9 cc or 1.1 cc tumor size) nor is the cycle rate necessarily exact (i.e. could be any value ≥a 4 day cycle and ≤a 20 day cycle) around the transition point. The further one can get all tumors below the 1 cc size, the more accurately a 4 day homogenous cycle rate can be insured, which in turn translates to increased curative probability.

Figure 8E:
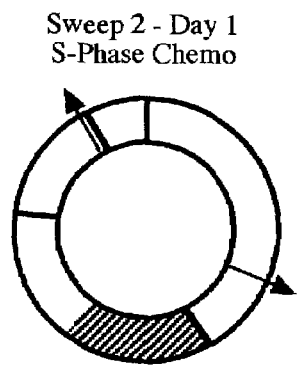
Figure 8F:
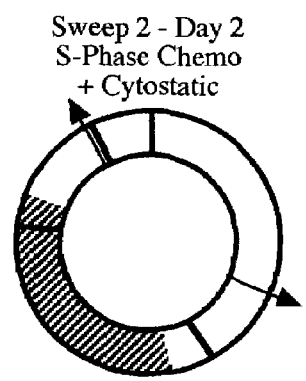
Figure 8G:
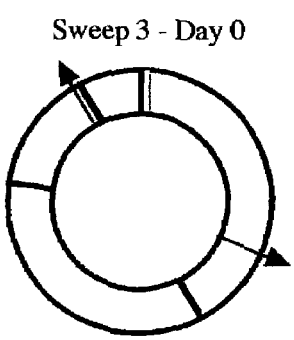
Figure 8H:
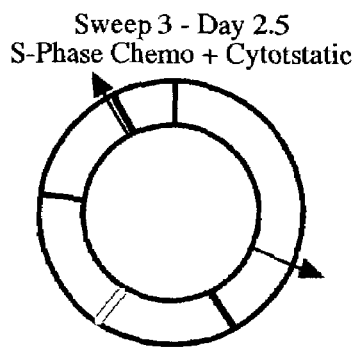
Figure 8I:
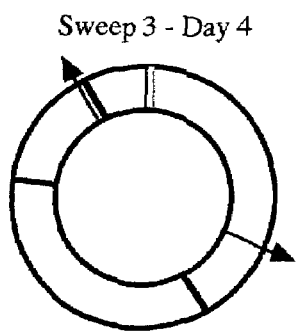

Phase Compressing Regimen for Example 2:

The Phase Compressing Regimen for use in Example 2 is the same as for Example 1 and is diagrammatically represented in FIGS. 8d-8f for the first sweep of Phase Compressing Chemo and FIGS. 8g-8i for all sweeps thereafter. The regimen comprises 10 consecutive sweeps.

The point of the additional sweeps are not only to increase Skipper log kill probabilities previously discussed, but to reduce the probability of a single survivor from non uniformities in resumption of cycling or infrequency of corroborative monitoring for resumption of cycling.

Alternate Phase Compressing Regimen for Example 1 or 2:

Six Phase Compressing Sweeps are used, however on the second and all subsequent sweeps (FIGS. 8g-8i) a conventional 7 consecutive day S-Phase cytotoxic cycle is administered on Day 0, 1, 2, 3, 4, 5, 6 and the cytostatic is administered starting on Day 5.

The point of the more frequent cytotoxic administrations is to provide for a larger safety margin for potential non uniformities in resumption of cell cycling. As an example, if daily PET scans are used and reveal resumption of cycling, the potential exists that the cycling may have started the previous day. Likewise, some cells may not resume cycling for another day. The more frequent administration provides greater coverage over larger range of non uniformities in resumption of cell cycling as well as allowing for less frequent monitoring for resumption of cell cycling. The cytostatic is used to re-aggregate any potential surviving cells, prevent any tumor growth prior to the next sweep of the regimen, and allow for hematologic recovery the 7 day regimen.

The point of this example is also to illustrate the innumerable variations and tradeoffs possible in a Phase Compressing Regimen. The importance is to note the primary difference from prior art in that the cytostatic in not used concurrently with the cytotoxic as part of combination chemotherapy. Under present invention the cytostatic is used in conjunction with a cytotoxic, with deliberately timed administrations and discontinuations of the cytostatic relative to the cytotoxic, in a manner that shuts the cancer off at a desired time and allows the cancer to restart cycling at a desired time, which in turn keeps the cancer synchronized to subsequent cytotoxic administrations.

EXAMPLE 3

Multiple Large Tumors

The patient presents with a non endocrine dependent 5 cc tumor in the lung, a 3 cc tumor in the liver, a 1 cc tumor in the kidney and it is suspected there are one or more undetected metastatic sites where the tumor is too small to be detected yet. It is determined the cancer has a 3+ level of HER2 overexpression as measured by prior art immunohistochemical assessment methods. The cancer cells are determined to have a 4 day cell cycle rate below the 1 cc level and 20 days above the 1 cc level.

Conforming Regimen for Example 3:

Under present invention two sweeps are required for the conforming regimen to insure all cells are at the fastest cycling rate prior to chemotherapy.

First Sweep: On day 0 and day 6, a high S-Phase kill rate cytotoxic chemo (e.g. 100 mg/m2 of irinotecan, 150 mg/m2 etoposide, or other suitable S-Phase chemotherapeutic) is administered. On day 3.5, a intravenous infusion loading dose of 4 mg/kg of the cytostatic agent Trastuzumab is administered followed by a 2 mg/kg maintenance dose in one week.

Second Sweep Where Day 0 is when the cells resume cycling from the First Sweep, 100 mg/m2 of Etoposide is administered on Day 1, 2, 3, and 9. On day 7, a intravenous infusion loading dose of 4 mg/kg of the cytostatic agent Trastuzumab is administered followed by a 2 mg/kg maintenance dose each week for 2 weeks.

The First Sweep is the same as that used in Example 1 and depicted in FIGS. 7a-7d and is designed primarily for a 20 day cycle. As in Example 1, approximately 61% of the 20 day cells are killed and eliminated in the sweep, leaving the 39% of survivors grouped between the start of the G Phase and the G1 checkpoint. After the First Sweep the tumor sizes are now: the 5 cc tumor is now 1.95 cc (i.e. 5 cc×0.39), the 3 cc tumor is now 1.17 cc, and the 1 cc tumor is somewhere around the 1 cc level as the first hit of chemo (32% reduction in tumor size) would have put it solidly into a 4 day cycle allowing it to eliminate the unviable cells and regrow most, if not all, of itself before being arrested on day 3.5 by the cytostatic.

The Second Sweep of the Conforming Regimen is designed for both a 4 and 20 day cycle, again not to kill all cells as required under chemotherapy, but to reduce and hold a tumor size to where a uniform cycling rate can be insured when the cells resume cycling. Although the reduction in tumor size from the First Sweep is likely large enough that most of the cells may well resume cycling at the 4 day rate, the regimen also covers the possibility some cells in more remote or more compressed areas of the tumor may still be at the 20 day rate. The leading edge of the 4 day cells will start reaching the midpoint of the S-Phase 1.1 days after resumption of cycling and the trailing edge will have reached the S-Phase midpoint 2.4 days after resumption of cycling (per FIG. 6b). Accordingly, the 4 day cells would have received one full chemotherapeutic sweep because of the cytotoxic administrations on Day 1, 2, 3 which would result in a 99% kill rate of the 4 day cells. The leading edge of any 20 day cells will start reaching the S-Phase midpoint in 5.5 days and the trailing edge would reach midpoint by 12.2 days (FIG. 6a). The cytostatic on day 7 allows all 20 day cycling cells to move past the G1 checkpoint (i.e. 6.7 days from start of G Phase to G1 checkpoint for a 20 day cell per FIG. 6a), however an earlier suitable time for administration of cytostatic may have been used as it is not a requirement of a Conforming Regimen to kill all cells. On Day 8.9 following resumption of cycling, the midpoint of the 20 day cells trapped in the G-Phase at the start of Sweep 2 will be at the midpoint of the S-Phase, or roughly 95% of the originally trapped cells will now be somewhere in the S-Phase (i.e. 6.4 day S-Phase duration+6.7 day G Phase start point to G1 checkpoint=95% overlap), hence the single cytotoxic administration on day 9 is employed. Other administrations of S-Phase cytotoxic may have been used (e.g. on day 6 and 12 or on days 6, 9, 12 following the midpoint rule, or any other suitable time) however since it is not a requirement of a Conforming Regimen to kill every last cell, preferred embodiment of present invention takes the route of minimizing systemic toxicity while still achieving desired therapeutic result.

The tumor sizes at the end of Second Conforming Sweep depend on the proportion of cells that would have been cycling at the 4 day rate and 20 day rate. The 4 day cells would have been reduced to 1% of their original population number, and then allowed to undergo one population division cycle before succumbing to cellular arrest resulting from the administration of the cytostatic on day 7, which would have restored them to 2% of their original population size. The 20 day cells were hit at 95% S-Phase overlap point with a 99% S-Phase cytotoxic which would imply a 94% kill rate, and making allowance for non uniformities in resumption of cycling and the single administration, the kill rate has been reduced to 80% for illustrative purposes in this example, leaving 20% survivors. The cytostatic administered on Day 7 would have prevented any regrowth in the 20 day cells.

Using the absolute worst case scenario of 20% survivors, would put the tumor sizes after the Second Conforming Sweep as follow: the 1.95 cc tumor would now be 0.4 cc (i.e. 1.95 cc×0.2), the 1.17 cc tumor would now be 0.23 cc, and the 1 cc tumor would be 0.2 cc or less. All tumors are now at a size that Gompertzian related chemotherapeutic failure would be avoided in subsequent conventional chemotherapeutic regimens. Alternatively, a phase compressing regimen as previously described under present invention, would preferably be employed.

EXAMPLE 4

Endocrine Dependent HER2 Driven Cancer

A patient presents with a 2 cc HER2 driven tumor in the lungs which is endocrine receptor positive (ER+), having metastasized from a breast cancer originally surgically removed from the breast.

Conforming Regimen for Example 4:

The conforming regimen of Example 1 is used with the exception that estrogen is administered in conjunction with the regimen (i.e. starting sometime prior to or concurrently with first administration of cytotoxic and lasting about 11 days after administration of the G-Phase cytostatic).

Phase Compressing Chemotherapeutic Regimen for Example 4:

The phase compressing regimen of Example 1 is used with the exception that estrogen is administered on Day 0 and lasting for 3 days after administration of cytostatic for each sweep of the phase compressing regimen.

Figure 9A:
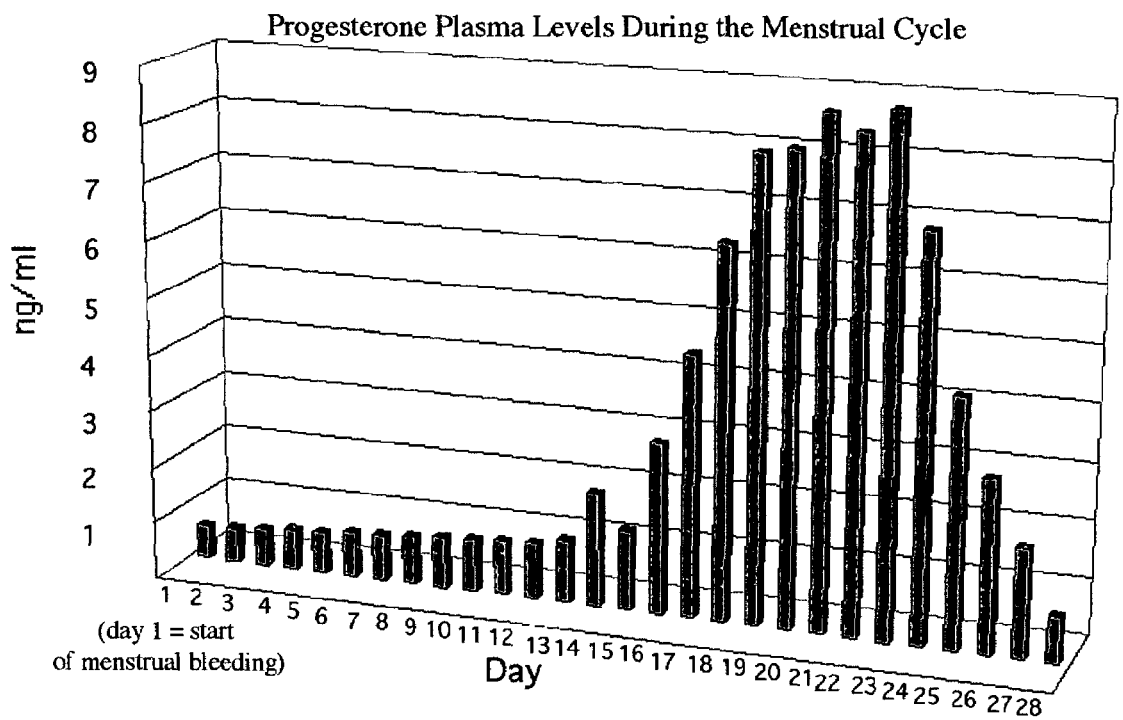
FIGS. 9a and 9b shows progesterone and estradiol plasma concentrations throughout the menstrual cycle.
Figure 9B:
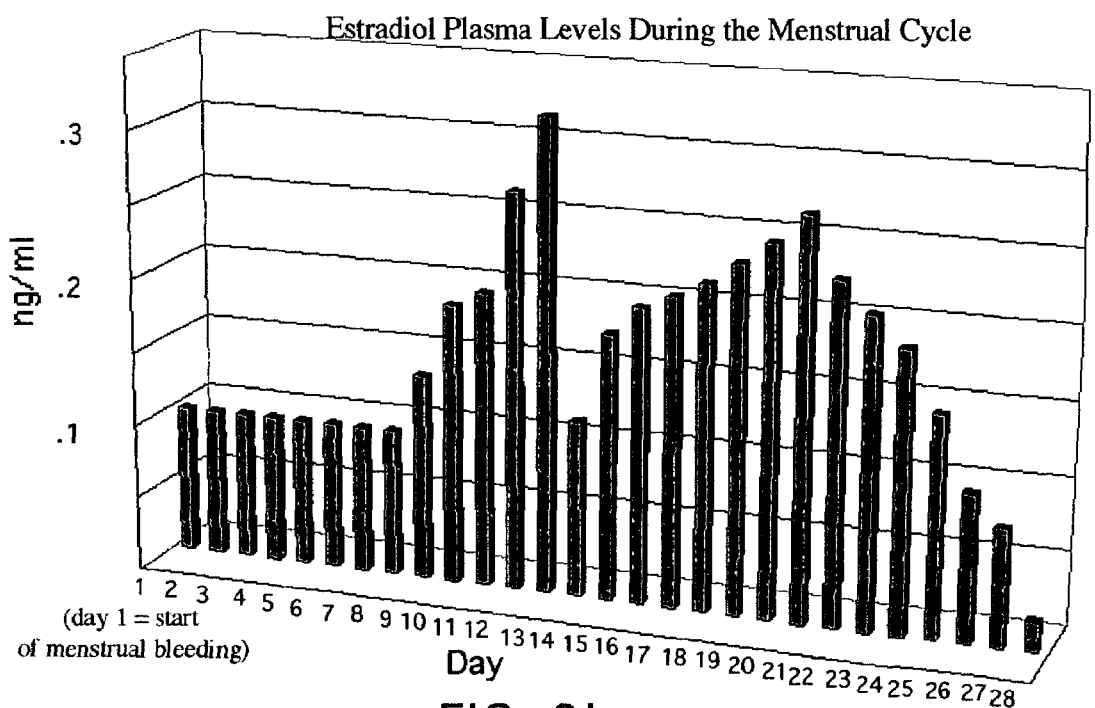

Overexpression of HER2, a member of the epidermal growth factor receptor super family, is found in several types of cancer including about 25% of breast cancer, 30% of non small cell lung cancers, and ovarian cancer. Endocrine dependence adds another level of synchronization complexity. Endocrine dependent tissues require endocrines produced by a distant organ to allow DNA transcription and hence the cell's progression through the cell cycle, a trait which is often retained by the cancer cell that arose from the underlying tissue. About two thirds of breast cancer are estrogen dependent (ER+) and between 40%-50% are progesterone dependent (PR+). Endocrine hormones dock with and activate appropriate intracellular endocrine receptors which in turn activate or upregulate DNA transcription (FIG. 5). In the absence of hormone, an inhibitory protein (e.g. Hsp 90) binds to the receptor and covers the DNA binding/dimerization domain. Hormone binding causes a conformational change in the receptor that results in the dissociation of the inhibitory protein, formation of homodimers, entry of the homodimers into the nucleus and binding to the palindromic DNA response element, upregulating DNA transcription. Indigenous hormone levels can fluctuate significantly throughout the menstrual cycle, with progesterone peaking at 9 times baseline at a certain point and estradiol peaking at 3 times baseline at a certain point (FIG. 9a and FIG. 9b). Hormones such as estrogen cause the transcription of proteins required for DNA replication. Accordingly, they can slow down or speed up a cell's progression through the S-Phase, which in turn can result in asynchronicity both Conforming and chemotherapeutic regimens.

The administration of hormones throughout the regimen accelerate the HER2 driven endocrine dependent cancer to a similar cell cycle rate and phase distribution as the HER2 driven non endocrine dependent cancer. Hormones for use are commercially available and administration methods are well defined under prior art (as disclosed in application Ser. No. 09/991,427 incorporated herein by reference). In the Conforming Regimen, the hormone administration duration of 11 days after administration of the cytostatic represents the time from the G1 checkpoint to the end of the M phase (for a 20 day cell per FIG. 6a), although a time of as little as 9 days could be used as that is the time it takes the same cells to clear the S-Phase. The 4 day duration for the Phase Compressed Regimen represents one entire cell cycle at the 4 day rate, insuring smooth progression through the end of the M-Phase.

Endocrine Accelerated/Downregulated Chemotherapeutic Regimen for Example 4

After the Conforming Regimen in Example 4, instead of using the Phase Compressing Chemotherapeutic Regimen, an Endocrine Accelerated/Downregulated Regimen may be employed as disclosed in application Ser. No. 09/991/427 and related claims 5-9. As an example, estradiol would be administered in conjunction with an S-Phase cytotoxic such as etoposide for 3 consecutive days (e.g. estradiol on Day 0-3 or Day 1-3 and cytotoxic on Day 1-3), followed by administration of an estrogen blocker such as anastrozole (starting after the terminal half life of the cytotoxic of Day 3 and continuing until the start of the next cycle). Subsequent sweeps would use estradiol on Day 0-2 and the S-Phase cytotoxic on Day 0-2, followed again by the endocrine blocker.

Endocrine Accelerated/Downregulated Conforming Regimen for Example 4

Endocrine blockers/downregulators such as anastrozole or tamoxifen could be used in place of the trastuzumab in the Conforming Regimen in Example 4, with the appropriate choice of cytotoxic(s) and timing adjustments commensurate with the switch from a G-Phase cytostatic to an S-Phase cytostatic. The Conforming Regimen would then be followed by an Endocrine Accelerated/Downregulated Chemotherapeutic Regimen as described above, or a Phase Compressing Regimen using trastuzumab, or a conventional chemotherapeutic regimen.

OTHER EMBODIMENTS AND ENVISIONED ENHANCEMENTS

The examples presented above represent only a few possibilities of using cytotoxics in conjunction with cytostatics, in a manner that prevent curative failure from Gompertzian acceleration, inter-cycle regrowth, and indigenous endocrine fluctuations. Many other embodiments are possible.

As an example, antibodies against HER2 receptors such as trastuzumab would not only be efficacious against cancers driven by overexpression of the HER2 receptor, but also cancers driven by overexpression of growth factors that bind to HER2 receptors.

The cytostatics used in the examples are only some representative examples of possible substances that could be used. Virtually any agent that can slow down or stop a given cancer mutation profile without a commensurate hematologic affect could be used.

The examples are presented as guidelines only and are not intended to imply these are the optimal combinations or optimal doses for use. Optimal dosages and timing as determined above would be further refined and corroborated in vivo in animal models and in human clinical trials as is customary under prior art methods.

It should not be inferred that the Gompertzian curve, cell cycle times, or phase distribution as presented and used will apply to all cancers equally. Variations in genetic mutation profiles driving the cancer, particularly in lower branches of growth pathways (e.g. overexpression of transcription proteins), will result in variations from models based on cancers driven by overexpression of growth factor receptors or growth factors, which more closely match normal mitogen driven cell cycle progression and phase distribution. Accordingly, as more precise Gompertzian curves and phase distributions are characterized for specific mutation profiles and cell types, the ability to keep chemotherapeutic regimens more precisely synchronized will provide additional benefits including cure rates approaching 100% as well as the ability to use chemotherapeutics with even shorter terminal half lives, virtually eliminating systemic toxicity.

In conclusion, applicant believes the examples demonstrate novelty and unobviousness and provide great utility over prior art. The compositions and methods of present invention prevent chemotherapeutic failure from Gompertzian acceleration, inter-cycle regrowth, and endocrine related phase distortions, a goal that has not only eluded but been largely overlooked by prior art, and as evidenced by the single digit cure rates under prior art for most advanced stage cancers as cited earlier in this application.

REFERENCES CITED

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th edition, McGraw Hill, 1998, Fauci, Braunwald, Isselbacher, Wilson, Martin, Kasper, Hauser, Longo. and 15th edition, McGraw Hill, 2001, Braunwald, Fauci, Kasper, Hauser, Longo, Jameson Referred to as "PDR" in this application: Physicians' Desk Reference, 54th edition, Medical Economics Company, Inc., 2000, Referred to as "BP" in this application: Biochemical Pathways, John Wiley & Sons, Inc. 1999, Gerhard Michal.

I claim:

1. A method of progressively reducing the size of a tumor or tumors over expressing human epidermal growth factor receptor proteins (HER2 tumors) comprising interlaced administrations of S-Phase specific cell cycle active cytotoxic chemotherapeutic or chemotherapeutics in therapeutically effective amounts to reduce tumor size and HER2 antibodies in therapeutically effective amounts to inhibit tumor regrowth between successive administrations of said cell cycle active cytotoxic chemotherapeutic or chemotherapeutics and for a period of time that does not interfere with the utility of successive administrations of said cell cycle active cytotoxic chemotherapeutic or chemotherapeutics.

2. The method of claim 1 wherein said HER2 antibodies are trastuzumab.

3. The method of claim 1 wherein when said HER2 tumor or tumors are also estrogen, progesterone, or testosterone dependent then estrogen, progesterone or testosterone is administered at a point in time prior to, or concurrent with, or both prior to and concurrent with, administration of said S-Phase specific cell cycle active cytotoxic chemotherapeutic or chemotherapeutics in therapeutically effective amounts to insure progression of said estrogen, progesterone, or testosterone dependent tumor or tumors through the cell cycle.

4. The method of claim 1 wherein when said HER2 tumor or tumors are also estrogen, progesterone, or testosterone dependent then estrogen, progesterone or testosterone blockers or downregulators are administered in conjunction with said HER2 antibodies in therapeutically effective amounts to inhibit progression of said estrogen, progesterone, or testosterone dependent tumor or tumors through the cell cycle and estrogen, progesterone, or testosterone is administered at a point in time prior to, or concurrent with, or both prior to and concurrent with, administration of said S-Phase specific cell cycle active cytotoxic chemotherapeutic or chemotherapeutics in therapeutically effective amounts to insure progression of said estrogen, progesterone, or testosterone dependent tumor or tumors through the cell cycle.

* * * * *

UNITED STATES PATENT AND TRADEMARK OFFICE
CERTIFICATE OF CORRECTION

PATENT NO. : 7,309,486 B1
APPLICATION NO. : 10/295600
DATED : December 18, 2007
INVENTOR(S) : Mark Zamoyski It is certified that error appears in the above-identified patent and that said Letters Patent is hereby corrected as shown below:

On the title page (57) replace the Abstract with the following:

--The present invention discloses that prior art combination chemotherapy protocols for HER cancers (human epidermal growth factor receptor overexpression driven cancers) that employ concurrent administration of HER blockers and phase specific cell cycle active cytotoxics result in antagonistic action between the two classes of drugs in a manner that prevents function of all but the first administration of the phase specific cell cycle active chemotherapeutic. The present invention provides protocols that allow the two classes of chemotherapeutics to function synergistically. Prior art protocols also ignore endocrine dependence of HER cancers. The present invention discloses protocols for HER cancers that are also endocrine dependent in a manner that provides dual action by using both HER antibodies and endocrine blockers/downregulators and insures function of S-Phase cytotoxics by administration of endocrines prior to administration of the S-Phase cytotoxic.--

Signed and Sealed this

Twenty Second Day of April, 2008

JON W. DUDAS
*Director of the United States Patent and Trademark Office*